(12) United States Patent
Mahadevan-Jansen et al.

(10) Patent No.: US 9,023,089 B2
(45) Date of Patent: May 5, 2015

(54) SYSTEM AND METHODS FOR OPTICAL STIMULATION OF NEURAL TISSUES

(75) Inventors: Anita Mahadevan-Jansen, Nashville, TN (US); Jonathon D. Wells, Seattle, WA (US); E. Duco Jansen, Nashville, TN (US); Peter E. Konrad, Old Hickory, TN (US); Changquing C. Kao, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 512 days.

(21) Appl. No.: 13/117,850

(22) Filed: May 27, 2011

(65) Prior Publication Data

US 2014/0024902 A1    Jan. 23, 2014

Related U.S. Application Data

(63) Continuation of application No. 11/071,060, filed on Mar. 3, 2005, now Pat. No. 7,951,181, which is a continuation-in-part of application No. 10/333,700, filed as application No. PCT/US01/25501 on Aug. 15, 2001, now Pat. No. 6,921,413.

(60) Provisional application No. 60/225,690, filed on Aug. 16, 2000.

(51) Int. Cl.
*A61N 5/067* (2006.01)
*A61B 5/00* (2006.01)
*A61N 5/06* (2006.01)

(52) U.S. Cl.
CPC .......... *A61B 5/0048* (2013.01); *A61N 5/0601* (2013.01); *A61N 5/0613* (2013.01); *A61N 5/0619* (2013.01); *A61N 5/0622* (2013.01); *A61N 2005/0659* (2013.01); *A61N 2005/067* (2013.01)

(58) Field of Classification Search
USPC ...................................... 607/88–94
See application file for complete search history.

(56) References Cited

U.S. PATENT DOCUMENTS

| | | | |
|---|---|---|---|
| 3,900,034 A | 8/1975 | Katz et al. | |
| 4,287,488 A | 9/1981 | Brau et al. | |
| 4,917,084 A | 4/1990 | Sinofsky | |
| 4,966,144 A * | 10/1990 | Rochkind et al. | 607/89 |
| 4,972,420 A | 11/1990 | Villa | |
| 5,130,994 A | 7/1992 | Madey et al. | |
| 5,344,418 A | 9/1994 | Ghaffari | |
| 5,403,306 A | 4/1995 | Edwards et al. | |

(Continued)

OTHER PUBLICATIONS

Wells, J. et al., "Optical stimulation of neural tissue in vivo", Opt Lett, vol. 30, No. 5, pp. 504-506 (2005).

(Continued)

*Primary Examiner* — Aaron Roane
(74) *Attorney, Agent, or Firm* — Morris Manning & Martin LLP; Tim Tingkang Xia, Esq.

(57) ABSTRACT

The present invention, in one aspect, relates to a system for stimulating neural tissue of a living subject. The system comprises an energy source capable of generating optical energy, a connector having a first end and a second end capable of transmitting optical energy, and a probe operably coupled to the second end of the connector and having an end portion for delivering optical energy to a target neural tissue. In one embodiment, the energy source comprises a tunable laser.

39 Claims, 8 Drawing Sheets

(56) References Cited

U.S. PATENT DOCUMENTS

| | | | |
|---|---|---|---|
| 5,409,482 A | | 4/1995 | Diamantopoulos |
| 5,445,146 A | * | 8/1995 | Bellinger .................. 607/89 |
| 5,464,436 A | | 11/1995 | Smith |
| 5,514,126 A | | 5/1996 | Prescott |
| 5,616,140 A | | 4/1997 | Prescott |
| 5,738,680 A | | 4/1998 | Mueller et al. |
| 5,755,752 A | | 5/1998 | Segal |
| 5,860,972 A | | 1/1999 | Hoang |
| 5,871,522 A | | 2/1999 | Sentilles |
| 6,033,431 A | * | 3/2000 | Segal .................. 607/89 |
| 6,068,628 A | * | 5/2000 | Fanton et al. ............ 606/41 |
| 6,152,882 A | | 11/2000 | Prutchi |
| 6,200,311 B1 | | 3/2001 | Danek et al. |
| 6,233,480 B1 | | 5/2001 | Hochman et al. |
| 6,267,779 B1 | | 7/2001 | Gerdes |
| 6,273,905 B1 | | 8/2001 | Streeter |
| 6,330,388 B1 | | 12/2001 | Bendett et al. |
| 6,358,243 B1 | | 3/2002 | Esterowitz et al. |
| 6,375,651 B2 | | 4/2002 | Grasso, III et al. |
| 6,451,007 B1 | | 9/2002 | Koop et al. |
| 6,459,766 B1 | | 10/2002 | Srinivasan-Rao |
| 6,479,053 B1 | | 11/2002 | Jay |
| 6,482,199 B1 | | 11/2002 | Neev |
| 6,494,900 B1 | | 12/2002 | Salansky et al. |
| 6,629,948 B2 | | 10/2003 | Rockley et al. |
| 7,060,061 B2 | * | 6/2006 | Altshuler et al. .......... 606/3 |
| 7,115,120 B2 | | 10/2006 | Lin |

OTHER PUBLICATIONS

Hirase, H. et al., "Multiphoton stimulation of neurons", J Neurobiol, vol. 51, pp. 237-247 (2002).
Müller, M., "The cochlear place-frequency map of the adult and developing Mongolian gerbil", Hear Res, vol. 94, pp. 148-156 (1996).
Pearce, M., Richter, C.P., Cheatham, M.A., "A reconsideration of sound calibration in the mouse", J Neurosci Methods, vol. 106, pp. 57-67 (2000).
Balaban, P. et al., "He-Ne laser irridation of single identified neurons", Laser in Surgery and Medicine, vol. 12, pp. 329-337 (1992).
Black, R. C., Clark, G. M., Tong, Y. C., and Patrick, J. F., "Current distribution in cochlear stimulation", Ann NY Acad Sci., vol. 405, pp. 137-145 (1983).
Blamey, P. J., Pyman, B. C., Gordon, M., Clark, G. M., Brown, A. M., Dowell, R. C., and Hollow, R. D., "Factors predicting postoperative sentence scores in postlinguistically deaf adult cochlear implant patients", Ann Otol Rhinol Laryngol., vol. 101, No. 4, pp. 342-348 (1992).
Busby, P. A. and Clark, G. M., "Pitch and loudness estimation for single and multiple pulse per period electric pulse rates by cochlear implant patients", J Acoust Soc Am., vol. 101, No. 3, pp. 1687-1695 (1997).
Busby P.A. et al., "Pitch perception for different modes of stimulation using the cochlear multi-electrode prosthesis", JASA, vol. 95, pp. 2658-2669 (1994).
Chatterjee, M. and Shannon, R. V., "Forward masked excitation patterns in multielectrode electrical stimulation", J Acoust Soc Am., vol. 103(5 Pt 1), pp. 2565-2572 (1998).
Collins, M. M., Hawthorne, M. H., and el-Hmd, K., "Cochlear implantation in a district general hospital: problems and complications in the first five years", J Laryngol Otol., vol. 111, No. 4, pp. 325-332 (1997).
Dorman M.F. et al., "The recognition of sentences in noise by normal-hearing listeners using stimulations of cochlear-implant signal processors with 6-20 channels", JASA, vol. 104, pp. 3583-3585 (1998).
Dorman M.F. et al., "Speech intelligibility as a function of the number of channels of stimulation for signal processors using sine-wave and noise-band outputs", JASA, vol. 102, pp. 2403-2411 (1997).
Dowell R.C. et al., "Speech perception using a two formant22-electrode cochlear prosthesis in quiet and in noise", Acta Otolaryngol, vol. 104, pp. 439-446 (1987).

Edge, R. M., Evans, B. N., Pearce, M., Richter, C. P., Hu, X., and Dallos, P., "Morphology of the unfixed cochlea", Hear Res. vol. 124, No. 1-2, pp. 1-16 (1998).
Ehret G., Fisher R., "Neural activity and tonotopy in the auditory system visualized by c-fos gene expression", Brain Res., vol. 567, pp. 350-354 (1991).
Farber I.C., Grinvald A., "Identification of presynaptic neurons by laser photostimulation", Science, vol. 22, pp. 1025-1027 (1983).
Fichtel I., Ehret G., "Perception and recognition discriminated in the mouse auditory cortex by c-fos labeling", Neuroreport, vol. 10, pp. 2341-2345 (1999).
Fishman, K. E., Shannon, R. V., and Slattery, W. H., "Speech recognition as a function of the number of electrodes used in the SPEAK cochlear implant speech processor", J Speech Lang Hear Res., vol. 40, No. 5, pp. 1201-1215 (1997).
Friesen L.M. et al., "Speech recognition in noise as a function of the number of spectral channels: Comparison of acoustic hearing and cochlear implants", JASA, vol. 110, pp. 1150-1163 (2001).
Greenwood, D. D., "A cochlear frequency-position function for several species—29 years later", J Acoust Soc Am., vol. 87, No. 6, pp. 2592-2605 (1990).
Holmes, A. et al., "The effects of varying the number of cohlear implant electrodes on speech perception", Am J Otol, vol. 8, pp. 240-246 (1987).
Hu, X., Evans, B. N., and Dallos, P., "Transmission of basilar membrane motion to reticular lamina motion", Abtsr. Assoc. Res. Otolaryngol., 223 (1995).
Kral, A., Hartmann, R., Mortazavi, D., and Klinke, R., "Spatial resolution of cochlear implants: the electrical field and excitation of auditory afferents", Hear Res., vol. 121, No. 1-2, pp. 11-28 (1998).
Lin, X., "Action potentials and underlying voltage-dependent currents studied in cultured spiral ganglion neurons of the postnatal gerbil", Hear Res., vol. 108, No. 1-2, pp. 157-179 (1997).
Nagase, S. et al., "Changes in cochlear electrical stimulation induced c-fos expression in the rat inferior colliculus following deafness", Hear. Res., vol. 147, pp. 242-250 (2000).
Richter, C. P., Evans, B. N., Edge, R., and Dallos, P., "Basilar membrane vibration in the gerbil hemicochlea", J Neurophysiol., vol. 79, No. 5, pp. 2255-2264 (1998).
Saito, H. et al., "Fos-like immunoreactivity in the auditory brain stem evoked by bipolar intracochlear electrical stimulation: Effects of current level and pulse duration", Neuroscience, vol. 91, pp. 139-161 (1999).
Shannon, R. V., "Forward masking in patients with cochlear implants", J Acoust Soc Am., vol. 88, No. 2, pp. 741-744 (1990).
Shizuki, K. et al., "Expression of c-fos after noise-induced temporary threshold shift in the guinea pig cochlea", Neurosci. Lett., vol. 320, pp. 73-76 (2002).
Taylor, M. M. and Creelman, C. D., "Pest: Efficient estimates on probability functions", J Acoust Soc Am., vol. 41, pp. 782-787 (1967).
Uzdensky, A.B., Savransky, V.V., "Single neuron response to pulse-periodic laser microirridation. Action spectra and two-photon effect", Journal of Photochenistry and Photobiology B: Biology, vol. 39, pp. 224-228 (1997).
von Békésy, G., "The course pattern of the electrical resistance in the cochlea of the guinea pig (electroanatomy of the cochlea)", JASA., vol. 23, pp. 18-28 (1951).
Wan, H. et al., "Fos imaging reveals differential neuronal activation of areas of rat temporal cortex by novel and familiar sounds", Eur J Neurosci, vol. 14, pp. 118-124 (2001).
Zhou, J.C., "An advanced clinical trial with laser acupuncture anesthesia for minor operations in the oromaxillofacial region", Lasers Surg Med, vol. 4, pp. 297-303 (1984).
Fritsch, G. and E. Hitzig, "Ueber die elektrische Erregbarkeit des Grosshirns", Archiv Anatomie, Physiologie, und Wissenschaftliche Medicin, 37, pp. 300-332 (1870).
Geddes, L.A. and Bourland, J.D., "Tissue stimulation: theoretical considerations and practical applications", Med Biol Eng Comput, vol. 23, No. 2, pp. 131-137 (1985).
Devinsky, O., "Electrical and magnetic stimulation of the central nervous system", Historical Overview. Adv Neurol, vol. 63, pp. 1-16 (1993).

(56) References Cited

OTHER PUBLICATIONS

Pudenz, R.H., "Neural stimulation: clinical and laboratory experiences", Surg Neurol, vol. 39, No. 3, pp. 235-242 (1993).
Vaquero, J, Manrique, M., Oya, S, & Bravo, G., "Tissue damage after chronic cerebellar stimulation", Acta Neurochirurgica, vol. 56, No. 3-4, pp. 183-190 (1981).
Burke, D., et al., "Intraoperative monitoring. The International Federation of Clinical Neurophysiology", Electroencephalogr Clin Neurophysiol Suppl, vol. 52, pp. 133-148 (1999).
Allegre, G, et al. "Cerebral tissue excimer laser photoablation. Preliminary in vivo studies in the rat brain", Proc. SPIE, 1882, pp. 388-392 (1993).
Bragard, D, Chen, ACN, and Plaghki, L., "Direct isolation of ultralate (c-fibre) evoked brain potentials by CO2 laser stimulation of tiny cutaneous surfaces in man", Neuroscience Letters, vol. 209, pp. 81-84 (1996).
Roux, F.E, Tremoulet, M., "Organization of language areas in bilingual patients: a cortical stimulation study", J Neurosurg., vol. 97, No. 4, pp. 857-864 (2002).
Geddes, L.A. and Bourland, J.D., "The strength-duration curve", IEEE Trans Biomed Eng., vol. 32, No. 6, pp. 458-459 (1985).
Edwards, G.S., et al., "Tissue ablation by a free-electron laser tuned to the amide II band", Nature, vol. 371, pp. 416-419 (1994).
Meyer and Hegmann, American Journal of Physiology, vol. 220, No. 5, pp. 1383-1387 (1971).
Khosrofian, J.M. and Garetz, B.A., Applied Optics, vol. 22, No. 21, pp. 3406-3410 (1983).
Dallos, P., "The auditory periphery: Biophysics and physiology", In Dallos, P. The auditory periphery: Biophysics and physiology, Academic Press: New York (1973).
Dallos, P. and Cheatham, M.A., "Compound action potential (AP) tuning curves", J Acoust Soc Am, vol. 59, pp. 591-597 (1976).
Derbyshire, A.J. and Davis, H., "The action potential of the auditory nerve", Am. J. Physiol., vol. 113, pp. 476-504 (1935).
Egan, J. and Hake, P., "On the masking pattern of a simple auditory stimulus", JASA, vol. 22, pp. 622-630 (1950).
Plomp, R., "Detectability threshold for combination tones", JASA, vol. 37: pp. 1110-1123 (1965).
Richter, C.P., Koch, D.B., Micco, A.G., "Long-term deafened Gerbils: Relationship between Cochlear Physiology and Spiral-Ganglion-Cell Survival", Assoc Res Otolaryngol, vol. 26, p. 767 (2003).
Small, A.J., "Pure tone masking", JASA, vol. 31, pp. 1619-1625 (1959).
Tasaki, I., "Nerve impulses in individual auditory nerve fibers in guinea pig", J. Neurophysiol., vol. 17, pp. 97-122 (1954).
Vogten, L.L., "Low-level pure-tone masking: comparison of tuning curves obtained with simultaneous and forward masking", JASA, vol. 63, pp. 1520-1527 (1978).
Vogten, L.L., "Simultaneous pure tone masking: The dependence of masking asymmetries on intensity", JASA, vol. 63, pp. 1509-1519 (1978).
Wegel, R.L. and Lane, C.E., "The auditory masking of one pure tone by another and its probable relation to the dynamics of the inner ear", Phys. Rev., vol. 23, pp. 266-285 (1924).
Allegre, G., Avrillier S., "Stimulation in the rat of a nerve fiber bundle by a short UV pulse from an excimer laser" Neurosci Lett, vol. 180, pp. 261-264 (1994).
Friauf E., "Tonotopic order in the adult and developing auditory system of the rat as shown by c-fos immunocytochemistry", European journal of Neuroscience, vol. 4, pp. 798-812 (1992).
Gleich O., Stutz J., "Age-dependent effects of the onset of a conductive hearing loss on the volume of the cochlear nucleus subdivisions and the expression of c-fos in the mongolian gerbil (*Meriones unguiculatus*)", Audiol Neurootol, vol. 2, pp. 113-127 (1997).

Kilney, P. et al., "Effects of channel number and place of stimulation on performance with the cochlear corporation multichannel implant", Am J Otol, vol. 13, pp. 117-123 (1992).
Lawson, D. et al., "New processing strategies for multichannel cochlear prosthesis", Prog Brain Res, vol. 97, pp. 313-321 (1993).
Suesserman, M.F., Spelman, F.A., "Lumped-parameter model for in vivo cochlear stimulation", IEEE Trans Biomed Eng, vol. 40, pp. 237-245 (1993).
Turner, C.W. et al., "Use of temporal envelop cues in speech recognition by normal and hearing-impaired listeners", JASA, vol. 97, pp. 2568-2576 (1995).
van den Honert, C. and Stypulkowski, P. H., "Single fiber mapping of spatial excitation patterns in the electrically stimulated auditory nerve", Hear Res., vol. 29, No. 2-3, pp. 195-206 (1987).
Walker, J., "Reliev from chronic pain by low laser irridation", Neurosci Letter, vol. 43, pp. 339-344 (1983).
Walker, J. et al., "Laser therapy for pain of rheumatoid arthritis", Cin J Pain, vol. 3, pp. 54-59 (1987).
Wu, W.H., Ponnudurai, R., "Failure to confirm reported light evoked response of peripheral nerve to low power helium-neon light stimulus", Brain Res., vol. 401, pp. 407-408 (1987).
Xu, S.A. et al., "Profound hearing loss in the cat following the single co-administration of kanamycin and ethacrynic acid", Hear Res, vol. 70, pp. 205-215 (1993).
McGill, K.C, Cummins, KL, Dorfman, LJ, Berlizot, BB, Leutkemeyer, K, Nishimura, DG, Widrow, B. "On the nature and elimination of stimulus artifact in nerve signals evoked and recorded using surface electrodes", IEEE Trans Biomed Eng., vol. 29, No. 2, pp. 129-137 (1982).
Sunderland, S., "Anatomical features of nerve trunks in relation to nerve injury and nerve repair", Clin Neurosurg, vol. 17, pp. 38-62 (1970).
Kandel, E.R, Schwartz, JH, and Jessell, TM, editors, Principles of Neural Science, New York: McGraw-Hill, Health Professions Div., 4th edition (2000).
Diott, D & Fayer, M., J. Opt. Soc. Am. B. vol. 6, No. 5, pp. 977-994 (1989).
Edwards, GS, Johnson, B, Kozub, J, Tribble, J & Wagner, K., Opt, Engng, vol. 32, No. 2, pp. 314-319 (1993).
Thomsen, S., "Pathologic analysis of photothermal and photomechanical effects of laser-tissue interactions", Photochemistry and Photobiology, vol. 53, No. 6, pp. 825-835 (1991).
Chistovich, L.A., "Frequency characteristics of masking effects", Biofisika, vol. 2, pp. 749-755 (1957).
Zwicker, E., "On a psychoacoustical equivalent of tuning curves", In: Zwicker E, Terhardt E, editors. Facts and models in hearing. Springer-Verlag: New York, pp. 132-141 (1974).
Niemz, M.H., Laser Tissue interactions. Springer: New York, 1996.
Song, J.K., Abou-Khalil, B., Konrad, P.E., "Intraventricular monitoring for temporal lobe epilepsy: report on technique and initial results in eight patients", J Neurol Neurosurg Psychiatry, vol. 74, No. 5, pp. 561-565 (2003).
Cruccu, G and Romaniello, A., "Jaw opening reflex after CO2 laser stimulation of the perioral region in man", Experimental Brain Research, vol. 118, pp. 564-568 (1998).
Ueno, H, Kaneko, K, Taguchi, T, Fuchigami, Y, Fujimoto, H, Kawai, S., "Endoscopic carpal tunnel release and nerve conduction studies", Int Orthop., vol. 24, No. 6, pp. 361-363 (2001).
Starr, P.A., "Placement of deep brain stimulators into the subthalamic nucleus or Globus pallidus internus: technical approach", Stereotact Funct Neurosurg., vol. 79, No. 3-4, pp. 118-145 (2002).
Cheong, W.F., Prahl, S.A, Welch, A.J., "A review of the optical properties of biological tissues", IEEE J Quant Electron, vol. 26, pp. 2166-2185 (1990).

\* cited by examiner

SYSTEM AND METHODS FOR OPTICAL STIMULATION OF NEURAL TISSUES

CROSS-REFERENCE TO RELATED PATENT APPLICATION

This application is a continuation of, and claims benefit of U.S. patent application Ser. No. 11/071,060, filed Mar. 3, 2005, entitled "System and Methods for Optical Stimulation of Neural Tissues" by Anita Mahadevan-Jansen et al., which is now issued as U.S. Pat. No. 7,951,181 and which itself is a continuation-in-part of U.S. patent application Ser. No. 10/333,700, filed Jan. 23, 2003, entitled "Methods and Devices for Optical Stimulation of Neural Tissues," by Anita Mahadevan-Jansen et al., the disclosure of which is incorporated herein by reference in its entirety, which is now issued as U.S. Pat. No. 6,921,413 and itself claims the benefit, pursuant to 35 U.S.C. §371, of International Patent Application Serial No. PCT/US01/25501, filed Aug. 15, 2001, entitled "Methods and Devices for Optical Stimulation of Neural Tissues," by Anita Mahadevan-Jansen et al., the disclosure of which is incorporated herein by reference in its entirety, which itself claims the benefit, pursuant to 35 U.S.C. §119(e), of provisional U.S. Patent Application Ser. No. 60/225, 690, filed Aug. 16, 2000, by Anita Mahadevan-Jansen et al., the disclosure of which is incorporated herein by reference in its entirety.

STATEMENT OF FEDERALLY-SPONSORED RESEARCH

This invention was made with Government support under Contract No. FA9550-04-1-0045 awarded by the United States Department of Defense. The Government has certain rights in the invention.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [5] represents the 5th reference cited in the reference list, namely, Song J. K., Abou-Khalil B., Konrad P. E., Intraventricular monitoring for temporal lobe epilepsy: report on technique and initial results in eight patients. J Neurol Neurosurg Psychiatry 74(5), 561-5 (2003).

FIELD OF THE INVENTION

The present invention relates generally to the stimulation of neural tissues. More specifically, the present invention relates to system and methods for stimulating neural tissues in vivo by optical irradiation.

BACKGROUND OF THE INVENTION

For over a century, the traditional method of stimulating neural activity has been based on electrical methods, which has undergone few modifications over the years and remains the gold standards to date [1-5]. Electrical stimulation is utilized to identify the connectivity and functionality of specific nerve roots to be selectively avoided or resected [13], to create a unique map of functional structures that varies among individuals [14,15] during brain tumor resection, and to restore function in disabled individuals. However, electrical stimulation is prone to electrical interference from the environment, high frequency artifacts associated with the electrical signal used, intrinsic damage caused by the electrodes used for stimulation themselves, population response due to the recruitment of multiple axons, which prevents simultaneous stimulation and recording of adjacent areas, and in general poor spatial specificity.

Therefore, a heretofore unaddressed need exists in the art to address the aforementioned deficiencies and inadequacies.

SUMMARY OF THE INVENTION

In one aspect, the present invention relates to a system for stimulating neural tissue of a living subject. The system comprises an energy source capable of generating optical energy, a connector having a first end and a second end capable of transmitting optical energy, wherein the first end of the connector is coupled to the energy source, and a probe operably coupled to the second end of the connector and having an end portion for delivering optical energy to a target neural tissue. When the probe delivers optical energy to the target neural tissue through the end portion, the end portion is positioned away from the target neural tissue such that there is a distance between the end portion and the target neural tissue. The target neural tissue comprises at least one nerve associated with a peripheral and/or a central nervous system of the living subject.

In one embodiment, the energy source comprises a tunable laser. The tunable laser comprises a pulsed infrared laser. In one embodiment, the connector comprises a body portion defining a channel extending from the first end to the second end, and at least one optical fiber housed in the channel. The connector further comprises a plurality of optical fibers housed in the channel, each of the plurality of fibers being capable of transmitting optical energy. The plurality of fibers form a bundle or an array. A knob can be used for tuning laser fluence of the tunable laser.

The connector further comprises a control wiring housed in the channel. In one embodiment, the control wiring controls the knob for tuning laser fluence of the tunable laser. In one embodiment, the probe further comprises a base portion and a casing for housing the base portion and the end portion. The probe is movable three dimensionally to selectively deliver optical energy to one or more neural fibers of the target neural tissue.

In another aspect, the present invention relates to a system for stimulating neural tissue of a living subject. The system comprises an energy source capable of generating optical energy and a delivering means coupled to the energy source for delivering optical energy to a target neural tissue. The delivering means is adapted for delivering optical energy to the target neural tissue at a distance away from the target neural tissue. In one embodiment, the energy source comprises a tunable laser. The tunable laser comprises a pulsed infrared laser.

In one embodiment, the delivering means comprises a connector having a body portion defining a channel extending from a first end to a second end, at least one fiber housed in the channel capable of transmitting optical energy, and a probe operably coupled to the second end of the connector and having an end portion for delivering optical energy to a target neural tissue. The delivering means further comprises one or more optical fibers housed in the channel. The one or more optical fibers form a bundle or an array. A knob may be used for tuning laser fluence of the tunable laser. The delivering means further comprises at least one control wiring housed in the channel and a selecting device coupled to the connector for selectively delivering optical energy through at least one of the plurality of fibers. In one embodiment, the control wiring controls the knob for tuning laser fluence of the tunable laser. In one embodiment, the system of the present invention further comprises a computer coupled to the selecting device for controlling the selecting device. The delivering means further comprises a movable stage that is coupled to the computer, wherein the probe is mounted to the movable stage so that the probe is movable with the movable stage three dimensionally to selectively deliver optical energy to one or more neural fibers of the target neural tissue. The delivering means further comprises driving means for moving the movable stage three dimensionally. In one embodiment, the probe further comprises a base portion and a casing capable of housing the base portion and the end portion. The probe is movable three dimensionally to selectively deliver optical energy to one or more neural fibers of the target neural tissue.

In another embodiment, the delivering means comprises a first optical means for directing the optical energy to a desired direction and a second optical means for focusing the optical energy directed by the first optical means to a target neural tissue, wherein the first optical means and the second optical means are positioned along an optical path. The first optical means comprises an optical reflector. The second optical means comprises an optical lens. The target neural tissue comprises at least one nerve associated with a peripheral and/or a central nervous system of the living subject.

In yet another aspect, the present invention relates to a method of optically stimulating neural tissue of a living subject, comprising the step of delivering optical energy to a target neural tissue at a distance away from the target neural tissue. The method further comprises the step of focusing the optical energy on the target neural tissue so that the target neural tissue propagates an electrical impulse, wherein focusing the optical energy occurs in an area with a diameter in a range from 10 micrometers to 1000 micrometers, more preferably around 600 micrometers. The method further comprises the step of delivering optical energy in a motion to the target neural tissue. In one embodiment, the target neural tissue receives the optical energy for an amount of time sufficient to initiate action potential propagation within the target neural tissue. The optical energy is generated by a tunable laser and/or a pulsed infrared laser. The optical energy comprises pulses of laser beam with pulse duration in a range from 1 µs to 10 ms, more preferably with pulse duration around 350 µs. The optical energy comprises a laser beam with a wavelength in a range from 0.5 µm to 10 µm, more preferably in the range from 1.2 µm to 5 µm. The optical energy is delivered with a repetition rate no more than 1,000 Hz, more preferably around 2 Hz. The optical energy comprises a laser beam with a radiant exposure no more than 5.0 J/cm$^2$, more preferably no more than 2.0 J/cm$^2$.

In a further aspect, the present invention relates to a method of stimulating neural tissue of a living subject, comprising the step of delivering at least one beam of radiation to a target neural tissue, wherein the beam of radiation has an intensity between a first intensity threshold and a second intensity threshold that is greater than the first intensity threshold. In one embodiment, the first intensity threshold is a stimulation threshold. The second intensity threshold is an ablation threshold. The ratio of the second intensity threshold to the first intensity threshold is in a range from 1 to 200, preferably in a range from 4 to 6 and is a function of a wavelength of the optical energy. In one embodiment, the beam of radiation comprises optical energy generated by a tunable laser and/or a pulsed infrared laser.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIG. 2a is a schematic diagram of a system 200 for optical stimulating neural tissue of a living subject according to another embodiment of the present invention.

FIG. 2b is a cross-sectional view of the connection of FIG. 2a.

FIG. 3a is a schematic diagram of a system for optical stimulating neural tissue of a living subject according to yet another embodiment of the present invention.

FIG. 3b is a cross-sectional view of the connection of FIG. 3a.

DETAILED DESCRIPTION OF THE INVENTION

Figure 1:
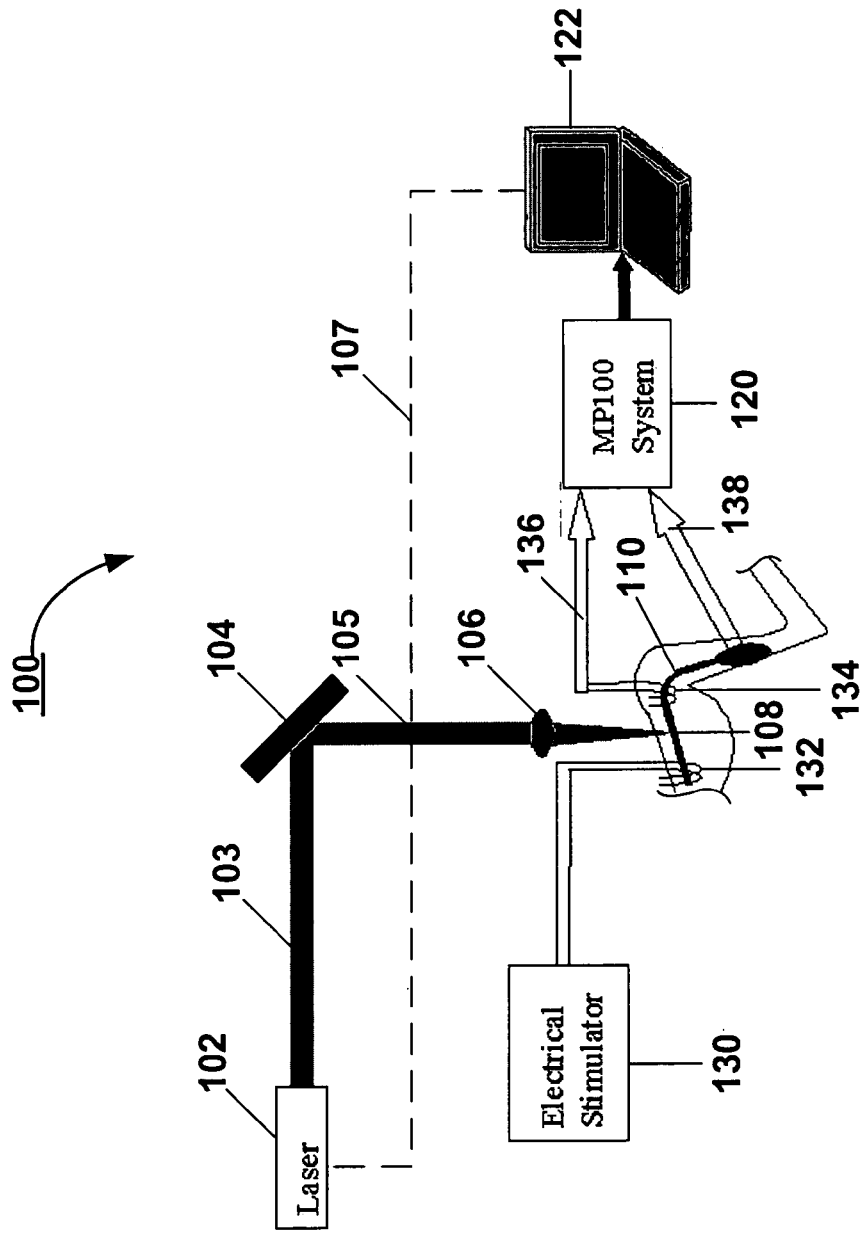
FIG. 1 is a schematic diagram of a system 100 for optical stimulating neural tissue of a living subject according to an embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing rat, monkey or the like.

FEL is an abbreviation for free electron laser.

CNAP is an abbreviation for compound nerve action potential.

CMAP is an abbreviation for compound muscle action potential.

As used herein "target neural tissue" is defined as any neural tissue or other excitable tissue including, but not limited to, the sciatic nerve of the leopard frog (Rana Pepieis), the sciatic nerve of mammals, brain and spinal cord tissue of mammals, and muscle tissue such as heart tissue of mammals.

As used herein "electrical impulse" is defined an electrical current applied via electrodes on the nerve to initiate an action potential in the neuron.

As used herein "stimulation effect" is defined as propagation of an electrical signal within neural or muscular tissue.

As used herein "nerve fiber" is defined as a portion of the neuron, namely the axon, which carries action potentials from one end of the neuron to the other. Many nerve fibers compose a peripheral nerve, such as the sciatic nerve of a leopard frog (Rana Pepiens) or a mammal.

As used herein, the term "radiant exposure" may be used interchangeably with the term "fluence."

As used herein "an area in a range of or a spot size of $d_1$ micrometers to $d_2$ micrometers," where $d_1$, $d_2$ are numbers, is synonymic to "an area with a diameter in a range of from $d_1$ micrometers to $d_2$ micrometers," as known to people who skilled in the art. For example, an area in a range of 50 micrometers to 600 micrometers is synonymic to an area with a diameter in a range of from 50 micrometers to 600 micrometers, corresponding to an area with a size in a range of 1964 micrometers$^2$ to 282,737 micrometers$^2$, estimated by using the formula of Area Size=$\frac{1}{4}\pi d^2$.

Northern Leopard Frog (Rana Pepiens) Sciatic Nerve Model System

Leopard frogs (Rana Pepiens) provide a widely accepted model system for studying the stimulation of a neural tissue. The frog sciatic nerve provides a robust nerve preparation not susceptible to ischemic changes. Additionally, frogs have a neuromuscular innervation similar to mammals, and extensive research has been carried out by the research community on the ability of neurons to conduct an electrical impulse (reviewed by Meyer and Hegmann, American Journal of Physiology, 220(5): 1383-7). Finally, leopard frogs (Rana Pepiens) provide a model system that is capable of withstanding temperature and humidity variations (Theophilidis and Pavlidou, Muscle & Nerve, 16(1):113-114).

Northern leopard frogs (Rana Pepiens) of sizes varying from 3-4 inches are selected so that the sciatic nerve may serve as the target neural tissue. The frog is pithed to make it brain dead, while still maintaining the vital body functions and the nerve conduction. Subsequent to being pithed, the animal is immobilized on a wax bed. The skin covering the hamstring muscle is cut in order to expose the muscle. Subsequently, an incision is made along the length of the hamstring muscle so as to expose the sciatic nerve. The sciatic nerve is freed from the connective tissue that connected it to the surrounding muscle. For experimental purposes, several pairs of electrodes were placed on the nerve. The first pair of electrodes is capable of electrical stimulation, the second pair of electrodes is capable of recording the nerve potentials, and the third pair of electrodes was pierced into the muscle that the sciatic nerve innervates so that muscle potentials may be recorded. Additionally, the sciatic nerve was kept moist at all times by using saline water.

The methods described herein have been used to stimulate a rat sciatic nerve. One of ordinary skill in the art understands the differences in the surgical procedure necessary to expose the rat sciatic nerve compared to the surgical procedure described above for the frog. The same method of optical stimulation was used for the rat nerve and frog nerve. Regarding the stimulation of the rat sciatic nerve, a wavelength of 4.4 micrometers, a pulse energy of 4.7 mJ, a spot size of 619 micrometers, and a pulse frequency of 2 Hz using the FEL were used. Optical stimulation was also tested using energy of 1.78 mJ or 2.39 mJ, and using wavelengths of 2.1 μm, 3.0 μm, 4.0 μm, 4.5 μm, 5.0 μm, and 6.0 μm.

Free Electron Laser

A free electron laser and delivery optics are used to generate and manipulate the optical energy. The optical energy transport system is maintained under rough vacuum. The optical energy is focused on the target neural tissue using focusing lenses (Vi Convex Lenses, f=300 mm) to a spot size of around 400 micrometers.

The response of the sciatic nerve to the optical energy stimulation is sensed using stainless steel needle electrodes that are placed under the sciatic nerve for compound nerve action potential recording. Additionally, the electrical response from the sciatic nerve is monitored by recording electrodes placed in the nerve downstream and innervated hamstring muscle. If the sciatic nerve conducts an electrical impulse, a tiny electrical signal can be detected from the nerve (CNAP) and a much larger electrical signal can be detected from the muscle (CMAP). The signals are recorded using the MP100 system from Biopac Systems (Santa Barbara, Calif.) that is combined electrical stimulation and recording unit. The nerve was electrically stimulated using S44 Grass electrical stimulator from Grass Instruments, Quincy, Mass.

Optical stimulation was performed using laser pulses with energy in the range from 0.2 mJ to 5 mJ with a spot size of 300-600 micrometers (fluence values varied from 0.2 J/cm$^2$ to about 10 J/cm$^2$). The minimum energy and therefore fluence required to stimulate the frog nerve to trigger a visible muscle twitch within was found to be minimum (0.6 J/cm$^2$) between 4 and 4.5 micrometers. The spot size of the optical energy was determined using the knife-edge method (J. M. Khosrofian and B. A. Garetz, Applied Optics, 22(21): 3406-3410, 1983). The laser pulses were focused onto the sciatic nerve using biconvex lenses. The laser pulse energy was varied using a polarizer. The information recorded on the MP100 system was displayed using the AcqKnowledge software.

The FEL was selected for use in the initial studies with this method since it has the following advantages. The FEL is tunable in wavelength from 2 to 10 micrometers. Thus, FEL offers the flexibility of providing various wavelengths in the infrared spectrum for use with the method provided herein. Other sources may be used to generate the necessary wavelength. In addition to any source that can generate wavelengths in the infrared portion of the spectrum, sources may include LED and LCD. FEL additionally provides micropulses, each about 1 picosecond in duration and having a repetition rate of about 3 GHz. The envelope of this pulse train forms a macropulse that is about 3-6 microseconds and can be delivered at a rate up to 30 Hz. As mentioned above, optical stimulation of the peripheral nerves employ pulse energies ranging from 0.2 mJ to 5 mJ in a spot size of around 500 micrometers.

Stimulation studies can also be performed using other sources. For example, if it is desired to use a wavelength around 4 micrometers, then a lead-salt laser, or an optical parametric oscillator (or amplifier) may be used.

OVERVIEW OF THE INVENTION

Among other things, applicants have invented a system for stimulating neural tissue of a living subject. The present invention is a novel technological breakthrough in neural tissue stimulation that uses low intensity infrared laser light to elicit compound nerve and muscle potentials and associated muscle contraction instead of electrical energy.

Although the gold standard of neural stimulation is by electrical means, it is well known that action potentials can be triggered in neurons using many different stimuli. Optical excitation can circumvent many of the limitations of electrical stimulation, including lack of spatial specificity and electrical artifacts that limit data analysis and make simultaneous excitation and recording from adjacent nerve fibers difficult [2, 6-8]. Optically induced neural action potentials are spatially precise, highly controlled and artifact-free, generated using energies well below tissue ablation threshold. The ratio of ablation threshold to stimulation threshold (safety ratio) is found to be inversely proportional to the tissue absorption and this ratio is highest at relative valleys of tissue absorption (4 and 2.1 μm) in the infrared. Thus, optical stimulation presents an innovative approach to contact-free neural activation that has major implications to clinical neural stimulation as well as basic neurophysiology and neuroscience.

Referring now to FIG. 1, a system 100 for optical stimulating neural tissue of a living subject according to an embodiment of the present invention is shown. The system has an energy source 102 capable of generating optical energy and a delivering means coupled to the energy source 102 for delivering optical energy to a target neural tissue 110. The delivering means is adapted for delivering optical energy to the target neural tissue at a distance away from the target neural tissue 110. In other words, the delivering means delivers optical energy to a target neural tissue in a contact-free manner. The energy source 102 in one embodiment is a continuously tunable, pulsed infrared laser. The laser has a λ range (NIR-IR) from 1.2 to 10 μm, a pulse duration in a range from 1 μs-10 ms, and repetition rates up to 1000 Hz. Other types of laser can also be utilized to practice the present invention. The energy source 102 is operably coupled to and controllable by a computer 122.

The delivering means has a first optical means 104 for receiving the optical energy from the energy source 102 along optical path 103 and then directing the optical energy along optical path 105 to a second optical means 106 for focusing the optical energy directed by the first optical means 104 to a target neural tissue 110. The optical energy arrives at the target neural tissue 110 at a selected spot 108 to cause stimulation. In the embodiment shown in FIG. 1, the first optical means is an optical reflector 104. The second optical means is an optical lens 106. The target neural tissue 110 comprises at least one nerve associated with a peripheral nervous system of the living subject.

In comparison, when an electrical stimulator 130, which is not a part of the system 100 and is shown in FIG. 1 for comparison with the present invention, is used to stimulate the target neural tissue 110, a stimulus is sent through stimulating electrodes 132 placed physically in contact with the target neural tissue 110 to elicit stimulation. The electrical stimulator 130, therefore, is not contact free and invasive. Sensing electrodes 134 are placed apart from the stimulation spot 108 and the stimulating electrodes 132 to receive the action potentials generated by either the optical or electrical stimulation. CNAP signals 136 and CMAP signals 138 responsive to the stimulation(s) and generated from the target neural tissue 110 are output to an MP100 system 120 (Biopac Systems, Santa Barbara, Calif.) for recording and processing, which is installed in the computer 122.

Referring now to FIGS. 2a and 2b, a system 200 for optical stimulating neural tissue of a living subject according to another embodiment of the present invention is schematically shown. The system 200 has an energy source 202 capable of generating optical energy, a connector 204 having a first end 205 that is coupled to the energy source 202 and a second end 207 capable of transmitting optical energy, and a probe 206 operably coupled to the second end 207 of the connector 204 and having an end portion 208 for delivering optical energy to a target neural tissue 250. When the probe 206 delivers a beam 209 of optical energy to the target neural tissue 250 through the end portion 208, the end portion 208 is positioned away from the target neural tissue 250 such that there is a distance, d, between the end portion 208 and the target neural tissue 250.

In one embodiment as shown in FIGS. 2a and 2b, the energy source 202 is a pulsed laser system. The connector 204 is flexible and has a body portion 210 defining a channel 211 extending from the first end 205 to the second end 207, and a plurality of fibers 212 housed in the channel 211. Each of the plurality of fibers is capable of transmitting optical energy and has a dimension with a 10-1000 micron diameter. The plurality of fibers 212 can form a bundle 220 or an array 222. The probe 206 has a base portion 216 and a casing 218 for housing the base portion 216 and the end portion 208. The casing 218 is sterile, can be metallic or plastic, and is disposable or reusable. The probe 206 is movable three dimensionally to selectively deliver optical energy to one or more neural fibers of the target neural tissue. The probe 206 is typically 8 cm in length and 1 cm in diameter. There is also a knob 203 on the probe 206 that is used to tune laser fluence in a range of 0-2.0 J/cm$^2$ with digital display. The connector 204 further has a control wiring 214 housed in the channel 211. In one embodiment, the control wiring 214 is controlled by the knob for tuning laser fluence. In use, a user can use his/her hand to position the probe 206 over a target neural tissue to perform the optical stimulation.

In one embodiment, optical energy from a tunable or fixed wavelength infrared laser is delivered to target neural tissue of a living subject via a probe that includes one or more optical fibers embedded in a fixed positioning means holding them in a fixed position relative to a nerve of the living subject. In this embodiment, activating individual optical fibers activates individual groups of neurons.

Referring now to FIGS. 3a and 3b, a system for optical stimulating neural tissue of a living subject according to yet another embodiment of the present invention is schematically shown. The system has an energy source 302 capable of generating optical energy and a delivering means coupled to the energy source 302 for delivering optical energy to a target neural tissue 350. The delivering means is adapted for delivering optical energy to the target neural tissue at a distance away from the target neural tissue. In the embodiment as shown in FIG. 3a, the energy source 302 is a pulsed laser system. The delivering means comprises a connector 304 that is flexible and has a body portion 310 defining a channel 311 extending from a first end 305 to a second end 307, one or more fibers 312 housed in the channel 311 capable of transmitting optical energy, and a probe 306 operably coupled to the second end 307 of the connector 304 and having an end portion 308 for delivering optical energy to a target neural tissue 350. The plurality of fibers 312 can form a bundle 340 or an array 342 with each fiber having a diameter in the range from 10-1000 micron. The delivering means further comprises a selecting device 316 operably coupled to the connector 304 to select one or more fibers from the plurality of fibers 312 to selectively deliver optical energy to a target neural tissue. The selecting device 316 allows one to adjust the intensity, the duration and the location of the optical stimulation without need to adjust the output of the energy source 302. The probe 306 further comprises a base portion 319 and a casing 318 capable of housing the base portion 319 and the end portion 308. The casing 318 is sterile, can be metallic or plastic, and is disposable or reusable. The probe 306 is movable three dimensionally to selectively deliver optical energy to one or more neural fibers of the target neural tissue. The probe 306 is typically 8 cm in length and 1 cm in diameter. There is also a knob 303 on the probe 306 that is used to tune laser fluence in a range of 0-2.0 J/cm$^2$ with digital display. The connector 304 further comprises a control wiring 314 housed in the channel 311. In one embodiment, the control wiring 314 is controlled by the knob for tuning laser fluence. A computer 322 is operably coupled to the selecting device 316 for controlling the selecting device 316. A movable stage 320 can be optionally coupled operably to the computer 322, wherein the probe 306 is mounted to the movable stage 320 so that the probe 306 is movable with the movable stage 320 three dimensionally to selectively deliver optical energy to one or more neural fibers of the target neural tissue. Driving means such as a motor driver can be utilized for moving the movable stage 320 three dimensionally.

Figure 2:
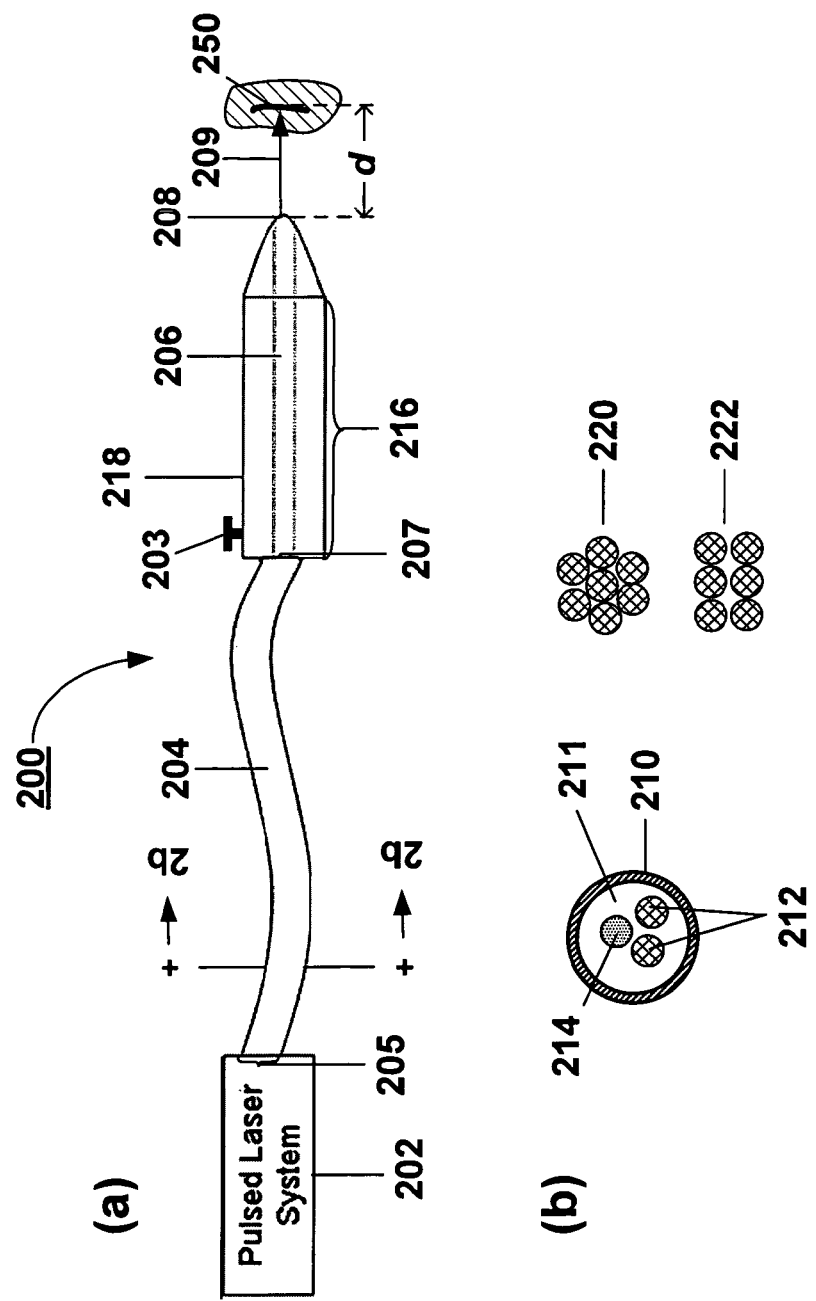
Figure 3:
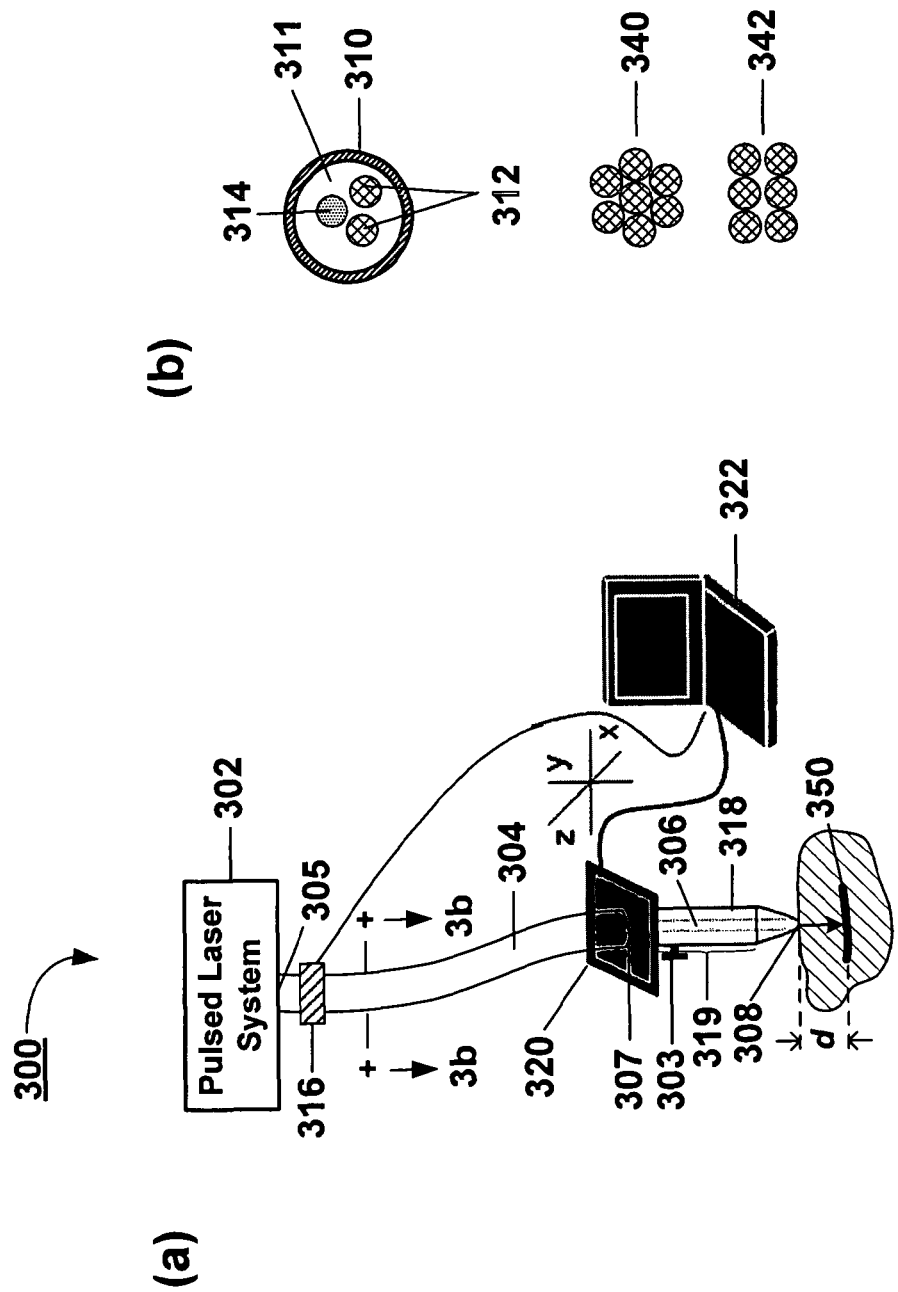

Note that although the embodiments as shown in FIGS. 2 and 3 have a multiple-fiber arrangement, respectively, a single fiber configuration can be used to practice the present invention as well.

While a pulsed laser system has been used in the embodiments set forth above, other types of lasers can also be utilized to practice the present invention.

METHODS, EXAMPLES AND IMPLEMENTATIONS

Without intent to limit the scope of the invention, exemplary methods and their related results according to the embodiments of the present invention are given below. Note again that titles or subtitles may be used in the examples for convenience of a reader, which in no way should limit the scope of the invention. Moreover, certain theories are proposed and disclosed herein; however, in no way they, whether they are right or wrong, should limit the scope of the invention.

Several exemplary experiments were conducted at the Vanderbilt University W. M. Keck Free Electron Laser Center and the Vanderbilt Biomedical Optics Laboratory in accordance with animal protocols approved by the Institutional Animal Care and Use Committee (IACUC).

Example 1 Nerve Preparation

Spraque-Dawley rats (300-350 g) and Leopard frogs (2-3 in.) were utilized for in vivo sciatic nerve preparations. The rats were anesthetized through intraperitoneal injection using a 50% urethane solution and maintained sedated for the duration of each experiment, while frogs were pithed so as to maintain vital body functions and nerve conduction during dissection and stimulation. The skin overlying the rat sciatic nerve was shaved and disinfected, and dissected to expose the main trunk of the sciatic nerve to the level of the knee where the nerve begins to branch. Nerves were stimulated 1 mm distal to the first branch point on the main sciatic nerve trunk from which a muscle response was elicited in the hamstring. The main branch was stimulated, proximal to the branch point, only for compound nerve action potential (CNAP) recordings in order to create space for the action potential to propagate and allow recording electrodes distal to the stimulation site.

Example 2 Laser Irradiation

When using the tunable FEL source, the laser beam was directed using a series of infrared optics and mirrors under vacuum to the experimental setup. The FEL operates in the 2-10 μm region, with a unique pulse structure consisting of a train of 1 μs micro-pulses within a 5 μs macro-pulse. The laser was operated at 2 Hz and a helium-neon laser beam at 632.8 nm was co-aligned to the IR-FEL beam and used as an aiming laser. The beam was then focused using a focusing lens (biconvex lens, f=300 mm) into a 500 µm hollow waveguide positioned slightly above the nerve sample. The small angle of divergence from the waveguide (6°) resulted in a spot size of 600 µm at the nerve. Laser pulse energy was varied by rotating a linear polarizer in the beam line. Optical stimulation was performed using laser pulses with radiant exposures from 0.3 J/cm$^2$ to just above 1 J/cm$^2$. Energies were measured using an energy meter (Molectron Inc).

A commercial Ho:YAG laser (Schwartz Electro Optics Inc.) was used to generate 2.12 µm irradiation. The laser beam was directly coupled into a 600 µm fiber that was placed directly above the nerve. Laser pulses with pulse duration of 350 µs were delivered at 2 Hz. Pulse energy fluctuations for each pulse were measured by directing 10% of the laser beam to the energy meter. Radiant exposures used to stimulate were roughly 1 J/cm$^2$.

Example 3 Electrophysiological Recording

Electrical stimulation and recording were performed using an MP100 system (Biopac Systems, Santa Barbara, Calif.). At the beginning of every stimulation experiment, the sciatic nerve response to electrical stimulation was recorded using voltage pulses of 0.3-0.6V at pulse duration of 5 µs. The nerve response was recorded using silver chloride wire electrodes placed on the nerve 15 mm from the stimulation site for CNAP recording and needle electrodes pierced into the hamstring muscle 45 mm from the stimulation site for CMAP recording. The system is controlled using proprietary software (Acqknowledge®), through a communication card and displayed on the computer screen. During optical stimulus, data acquisition was triggered using a TTL voltage pulse synchronized with the output of the laser. Data recording was initiated 1-2 ms prior to the stimulus to observe baseline electrical activity. The CNAPs and CMAPs evoked from optical and electrical stimulation were amplified by 1000× and filtered using a 5 KHz low pass filter to eliminate high frequency noise.

Example 4 Histology

Histological analysis was performed to assess tissue damage from optical stimulation using the Ho:YAG laser. In acute studies, radiant exposures well over the ablation threshold were used to generate a damage zone on the rat sciatic nerve in vivo for positive control with an adjacent stimulation zone with 10 laser pulses using various radiant exposures above stimulation threshold (n=10). An ablation zone was placed in an adjacent area with 20 laser pulses, with energies well above the ablation threshold. In survival studies, neural tissue was again activated using 10 pulses above threshold radiant exposures after which the muscle and skin were sutured and the animal was followed for a period of 3-5 days in order to assess any delayed neuronal damage and Wallerian degeneration (n=10). A sham procedure with no stimulation was performed in the contra-lateral leg as negative control in all procedures. After each experiment, the site of stimulation was marked with methylene blue, while the ablative lesions were marked with black India ink. The nerve was then excised, immediately placed in formalin, prepared into slides of 5 µm thick sections, and submitted for histological analysis using light microscopy and routine H&E tissue staining. Areas of coagulation, axonal disruption, and perineurium damage were assessed. These were reviewed by a pathologist, and a four point grading scheme (0—no visible thermal changes, 1—reversible thermal damage in perineurium, no nerve damage, 2—thermal damage in perineurium extending to the interface of the perineurium and the nerve, 3—thermal damage in perineurium and in nerve) was assigned to each specimen indicating extent of damage at the site of optical stimulation.

Example 5 Physiological Evidence of Response to Optical Stimulation

Figure 4:
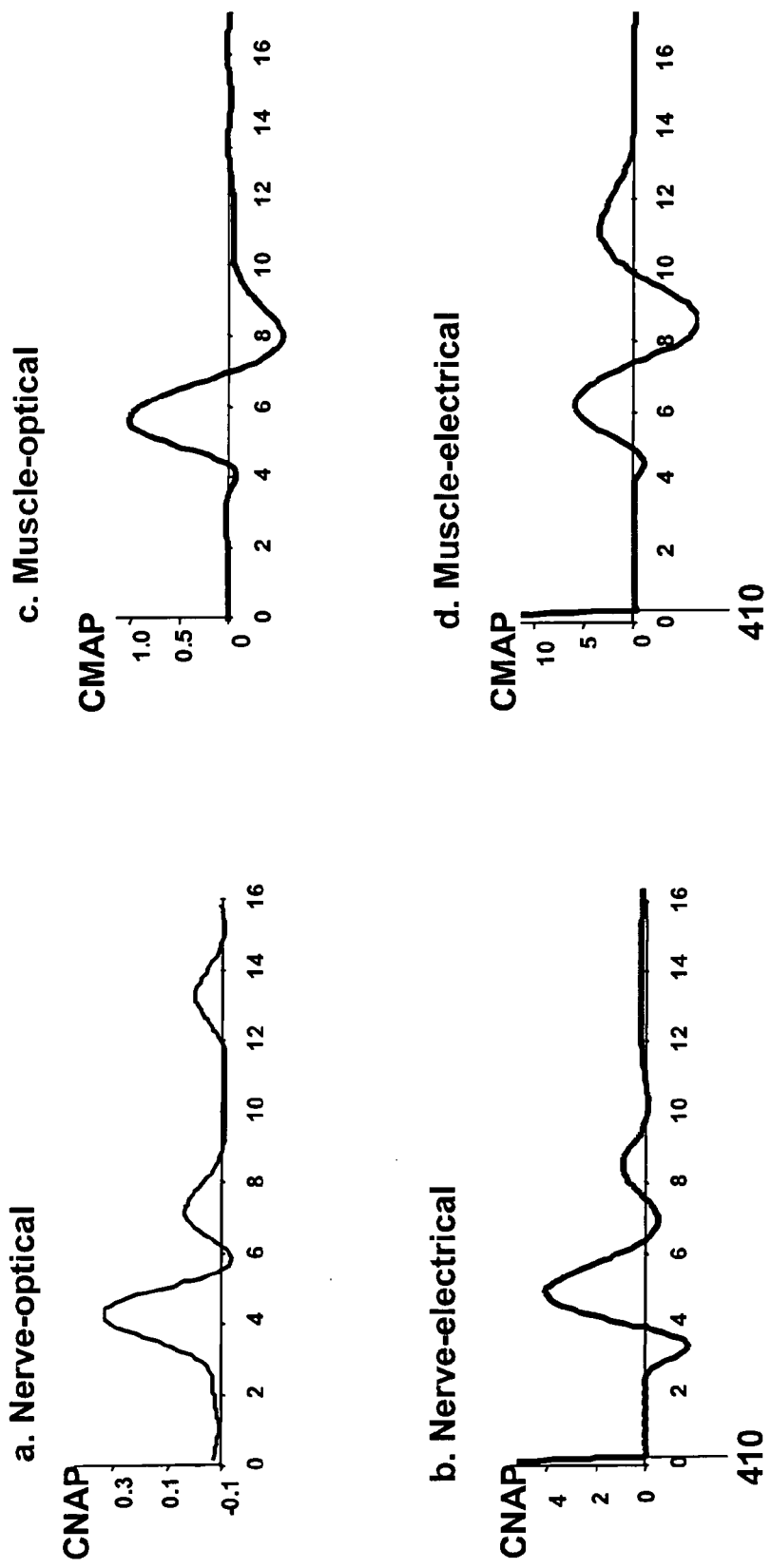
FIG. 4 displays compound nerve and muscle action potentials recorded from sciatic nerve in frog in vivo: (a) and (b) are compound nerve action potential (CNAP) recordings from optical and electrical stimulus, respectively; and (c) and (d) are compound muscle action potential (CMAP) recordings from optical and electrical stimulus, respectively.

Several studies were performed in vivo on the sciatic nerve of a frog as well as a rat model where neural activity was evoked using a pulsed infrared laser source and compared with electrical stimulation. Subsequent compound nerve (CNAP) and muscle action potentials (CMAP) were consistently observed and recorded using conventional electrical recordings as shown in FIG. 4. FIG. 4 describes compound nerve and muscle action potentials recorded from sciatic nerve in frog in vivo. FIG. 4a is CNAP recorded using optical stimulation at λ=4.0 µm. FIG. 4b is CNAP from electrical stimulation. FIG. 4c is Hamstring CMAP recorded using optical stimulation at λ=4.0 µm. FIG. 4d is Hamstring CMAP using electrical stimulation. Recordings reveal very little difference between optical and electrical stimulation in both the nerve and muscle recordings. The shape and timing of nerve and muscle potentials are similar for the two stimulation methods. FIGS. 4b and 4d elucidate an associated artifact 410 from electrical stimulation at t=0, not observed in optical stimulated recordings.

Several experiments were performed in vivo, initially on the frog sciatic nerve, and subsequently in mammals using a rat model, to verify the physiologic validity of optical stimulation. In order to confirm the direct stimulatory effect of low level optical energy, the nerve was optically isolated from its surrounding tissues using an opaque material and stimulated. A consistent evoked response was recorded indicating that the incident light is directly responsible for the CNAP and CMAP observed. Application of a depolarizing neuromuscular blocker (succinylcholine) resulted in a measurable CNAP and loss of CMAP, confirming the involvement of normal propagation of impulses from nerve to muscle upon optical stimulation. In addition, the similarity in the shape and timing of the signals from optical and electrical stimulus in FIG. 4 show that conduction velocities, represented by the time between the CNAP and CMAP, are equal. These traces imply the measured action potentials are identical regardless of excitation mechanism. It should be noted that the stimulation artifact 410 typically linked with traditional electrical methods is not observed in the optically elicited nerve and muscle responses, thus enabling simultaneous stimulation and recording from adjacent portions of a neuron; infeasible using electrical stimulation. These results explicitly prove that low-level pulsed infrared laser energy incident on the sciatic nerve can generate an artifact-free, physiologically valid compound nerve action potential, which propagates to the innervated muscle resulting in a visible muscle twitch that can be recorded using electromyography.

Experiments show the relationship between the optical radiant exposure [J/cm$^2$] and the amplitude of the evoked CNAP is similar to the strength curves observed in electrical stimulation, where the amplitude of the CNAP is proportional to the magnitude of stimulation [2,16,17]. Generally, individual nerve fiber diameters and excitation thresholds vary by small increments [18,19]. This implies that although individual axons within the nerve bundle obey an all or none response to a stimulus, the amplitude of the compound action potential is continuously graded due to the recruitment of axons. Thus, the CNAP and CMAP typically represent a population response to stimulation, made up of individual all-or-none responses from constituent axons [20].

Example 6 Spatial Selectivity in Optical Stimulation

Figure 5:
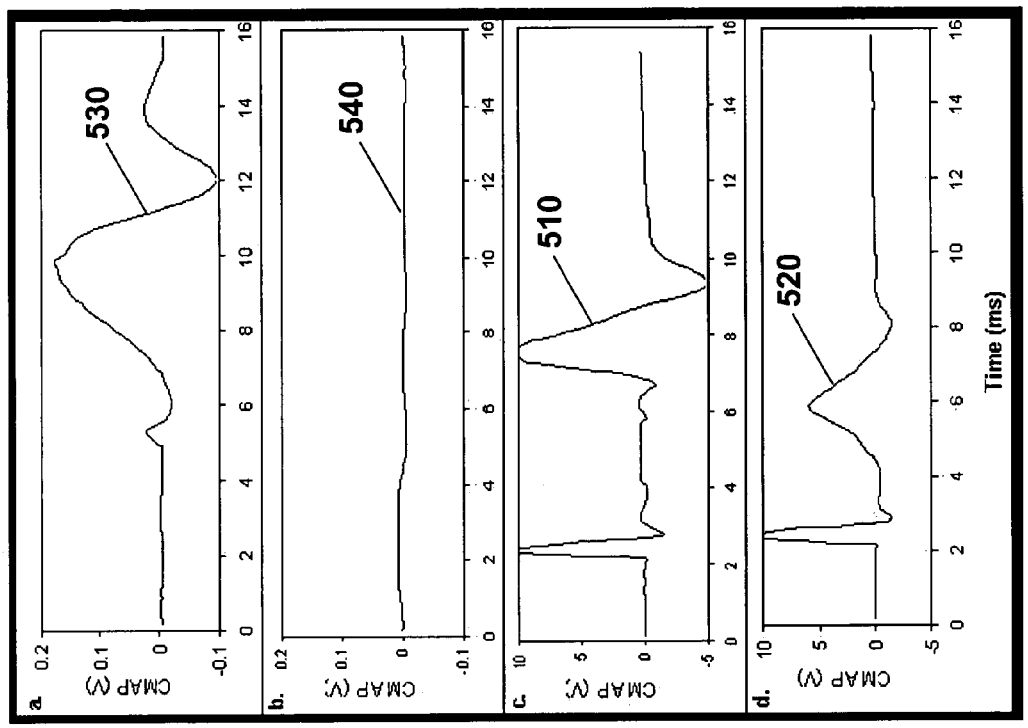
FIG. 5 provides spatial selectivity in optical stimulation compared with non-selective electrical activation in rat sciatic nerve: (a) a CMAP recording recorded upon optical stimulation of the fassicle innervating the quadriceps within the main branch of the sciatic nerve proximal to the first branch point with electrodes in the quadriceps; (b) a CMAP recording recorded upon optical stimulation of the fassicle innervating the quadriceps within the main branch of the sciatic nerve proximal to the first branch point with electrodes in the hamstring; (c) a CMAP recording recorded with electrical stimulation of the fassicle innervating the quadriceps within the main branch of the sciatic nerve proximal to the first branch point with electrodes in the quadriceps; and (d) a CMAP recording recorded from electrical stimulation of the fassicle innervating the quadriceps within the main branch of the sciatic nerve proximal to the first branch point with electrodes in the hamstring.

The precision and spatial specificity of optical excitation allows selective recruitment of motor axons within a nerve bundle, a phenomenon illustrated by comparison of the relative magnitudes of nerve and muscle potentials elicited from optical and electrical stimulation as shown in FIG. 5. With electrical stimulation a group twitch response is recorded, as all muscles innervated by a stimulated nerve branch or fascicle are activated in a non-selective manner. In contrast, the individual axons within a main nerve branch can be selectively stimulated to produce isolated, specific muscle contractions with optical excitation; a major advantage associated exclusively with this modality as shown in FIG. 5. FIG. 5 describes partial selectivity in optical stimulation compared with non-selective electrical activation in rat sciatic nerve. FIG. 5a is CMAP recorded upon optical stimulation of the fascicle innervating the quadriceps within the main branch of the sciatic nerve proximal to the first branch point with electrodes in the quadriceps. FIG. 5b is CMAP upon optical stimulation of the fascicle innervating the quadriceps within the main branch of the sciatic nerve proximal to the first branch point with electrodes in the hamstring. FIG. 5c is CMAP with electrical stimulation of the fascicle innervating the quadriceps within the main branch of the sciatic nerve proximal to the first branch point with electrodes in the quadriceps. FIG. 5d is CMAP from electrical stimulation of the fascicle innervating the quadriceps within the main branch of the sciatic nerve proximal to the first branch point with electrodes in the hamstring.

In FIG. 5 the non-selective activation due to electrical stimulation of the main branch of the sciatic nerve is compared with the selective activation due to optical stimulation of the main branch of the sciatic nerve. In electrical stimulation, a muscle response is generated equally in the quadriceps as well as hamstring muscles as shown by signal peaks 510 and 520, respectively. In optical stimulation, a specific fascicle innervating a specific muscle group, in this case quadriceps can be spatially selected and activated as shown by signal peak 530 and there is apparently no detectable stimulation in hamstring muscles as shown by a flat line 540. Such precision allows for targeted activation of individual axons within a nerve bundle, facilitating infinite resolution for spatial selectivity of optical stimulation. Thus, substantial clinical implications are manifest as this introduces an opportunity for partial nerve resection, infeasible with electrical stimulation, and the ability to map neural function with higher accuracy than is current practice.

Example 7 Safety for Optical Stimulation

In order to characterize the dependence of optical neural stimulation to laser wavelength and radiant exposures and to thus identify the optimal laser for consistent damage-free stimulation, a continuously tunable (2-10 μm), pulsed infrared laser source in the form of a free electron laser (FEL) was implemented [21-24] to stimulate the sciatic nerve in vivo in a rat. Wavelengths at or near relative peaks and valleys of tissue absorption (primarily governed by water absorption at these wavelengths) were chosen for this study to characterize stimulation thresholds compared to tissue absorption. While the FEL is an excellent source for gathering experimental data, it is neither easy to use nor clinically viable. Nevertheless, the experimental data gathered with this tunable light source, provides guidance towards the design of an appropriate and optimized turn-key bench top laser system for optical nerve stimulation.

Figure 6:
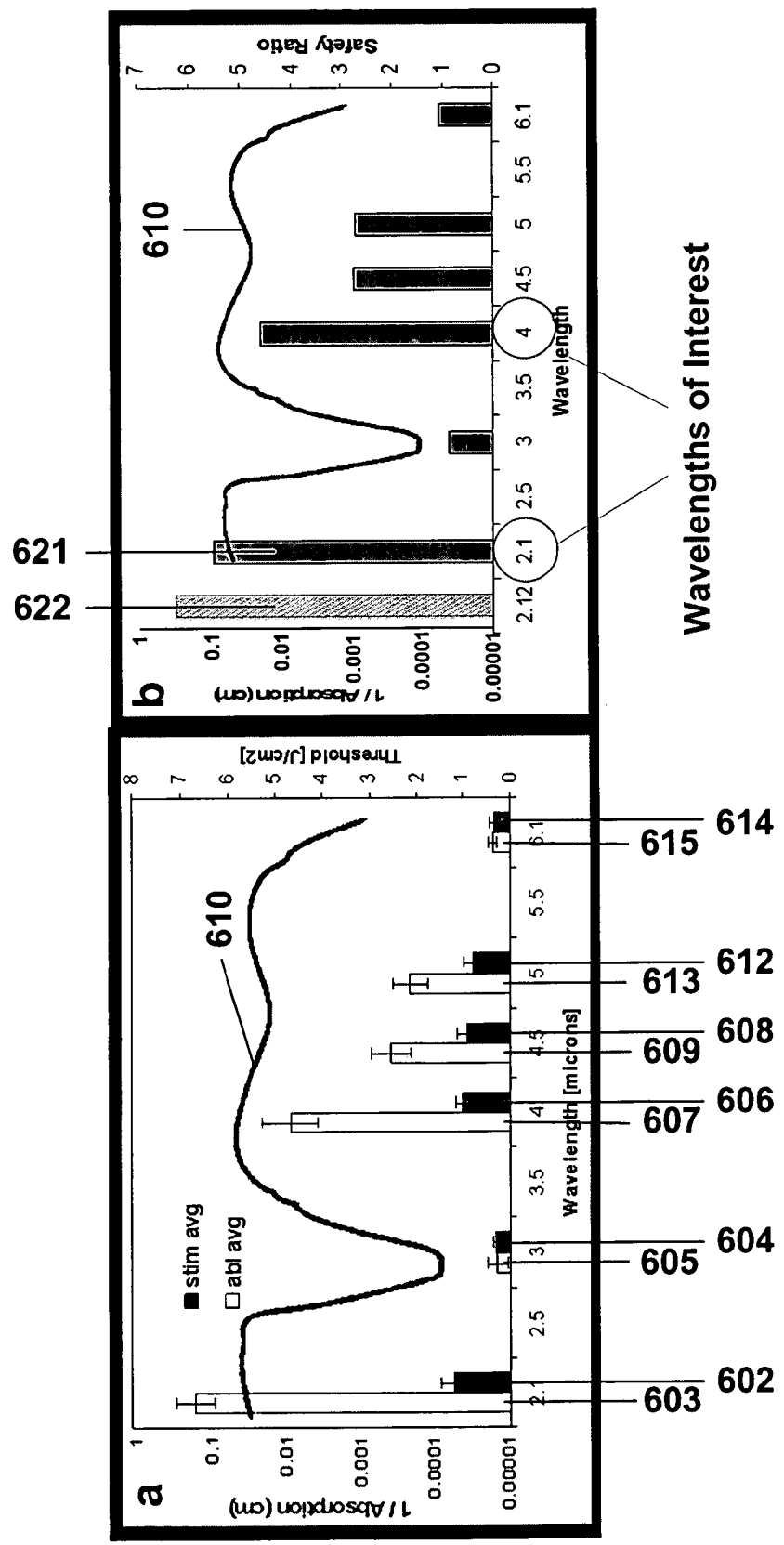
FIG. 6 shows the inversion of soft tissue absorption curve in connection with the safety of stimulation: (a) absorption obtained from an FEL employed to irradiate 4 different nerves for 3 trials each at 6 wavelengths, 2.1, 3.0, 4.0, 4.5, 5.0, and 6.1 µm, respectively, each near a relative peak or valley of water absorption (solid line); and (b) the safety ratio (stimulation/ablation threshold) for all wavelengths demonstrates wavelength dependence. The highest safety ratio, 5.5, occurs at a wavelength of 2.1 µm.

As shown in FIG. 6, the stimulation threshold exhibits a wavelength dependence that mirrors the inverse of soft tissue absorption curve 610 as measured with Fourier Transform Infrared (FTIR) spectroscopy. Various suitable wavelengths for optimal stimulation (maximum efficacy with minimum damage) can be inferred. The absolute stimulation threshold is lower at wavelengths with high absorption but it is also easier to ablate (less energy needed) at these wavelengths. Thus, a more useful indicator of optimal wavelengths to achieve damage-free stimulation is the safety ratio defined as the ratio of threshold radiant exposure for ablation to that for stimulation. This ratio identifies spectral regions with a margin of radiant exposures between excitation and damage and thus of safety. Results indicate that the highest safety ratios are obtained at 2.1 and 4.0 μm, which correspond to relative valleys in tissue absorption and equivalent absorption coefficients.

There are few lasers that emit light at 4.0 μm in wavelength, however, the Holmium:YAG (Ho:YAG) laser at 2.12 μm is commercially available and is currently used for a variety of clinical applications. Although the pulse structure of this laser differs from the FEL, light at this wavelength can be delivered via optical fibers facilitating the clinical utility of this laser. The Ho:YAG laser was successfully used for neural stimulation with average stimulation threshold radiant exposure of 0.32 J/cm$^2$ and an associated ablation threshold of 2.0 J/cm$^2$ (n=10), yielding a safety ratio of greater than 6.0. From the results obtained it can be conclude that clinically relevant wavelengths for optimal stimulation will not occur at peaks in tissue absorption because the energy required to produce action potentials within the nerve is roughly equal to the energy at which tissue damage occurs. It can also be predicted that absolute valleys in the absorption curve (i.e. visible and NIR region, 300-2000 nm) will not yield optimal wavelengths, because the low absorption will distribute the light through a large depth leading to insufficient energy delivered to the nerve fibers for an elicited response. Thus, the most appropriate wavelengths for stimulation of peripheral nerves occur at relative valleys in IR soft tissue absorption, which produce an optical penetration depth of a couple hundred micrometers, thus reaching the axon of these nerve bundles.

Referring now to FIGS. 6a and 6b, the inverse of soft tissue absorption curve as measured with Fourier Transform Infrared (FTIR) spectroscopy is indicated by solid line 610. FEL is employed to irradiate four different nerves for three trials each at six wavelengths, 2.1, 3.0, 4.0, 4.5, 5.0, and 6.1 microns, each near a relative peak or valley of water absorption of spectra 610. Stimulation threshold is the minimum radiant exposure for a visible CMAP occurring with each laser pulse. The variance in stimulation threshold was small, resulting in consistent stimulation across multiple samples as indicated by solid bars 602, 604, 606, 608, 612, and 614, corresponding to wavelengths 2.1, 3.0, 4.0, 4.5, 5.0, and 6.1 microns respectively. Ablation threshold is the minimum radiant exposure required for cavitation or ejection of material from the nerve with ten laser pulses delivered at 2 Hz. The variance in ablation threshold are indicated by open bars 603, 605, 607, 609, 613, and 615, corresponding to wavelengths 2.1, 3.0, 4.0, 4.5, 5.0, and 6.1 microns respectively. The safety ratio, defined as stimulation threshold divided by ablation threshold for all wavelengths demonstrates wavelength dependence. The highest safety ratio, 5.5, occurs at 2.1 microns, as indicated by a high bar 621. Tabletop Holmium: YAG laser operating at 2.12 microns exhibits the highest safety ratio, 6.25, of the wavelengths studied as indicated by the high bar at far left 622.

Example 8 Histology of Optically Stimulated Peripheral Nerves

Histological analysis was performed on excised nerves, both acutely and 3-5 days after stimulation, to assess and quantify the damage accrued within the nerve tissue following optical excitation with the Ho:YAG laser, identified as the optimal laser from safety ratio experiments. Irradiation sites were marked and sent for independent and blinded histological analysis [26,27]. The extent of histological damage at the site of optical stimulation was quantified in each acute specimen, while survival results were reported as with damage or no damage.

Results from the acute and survival studies demonstrate damage-free stimulation using an optical stimulus for neural activation. The results from the acute study indicate all ten nerves showed no signs of thermal damage to the nerve or perineurium at the site of stimulation with radiant exposures up to 2 times stimulation threshold. Histological examination from the survival study indicates no Wallerian degeneration or damage to the nerve or surrounding perineurium in 8 of the 10 specimens, using radiant exposures up to 2.5 times threshold. These histological findings suggest that nerves can be repetitively optically stimulated at or near threshold without causing any neural tissue damage.

Figure 7:
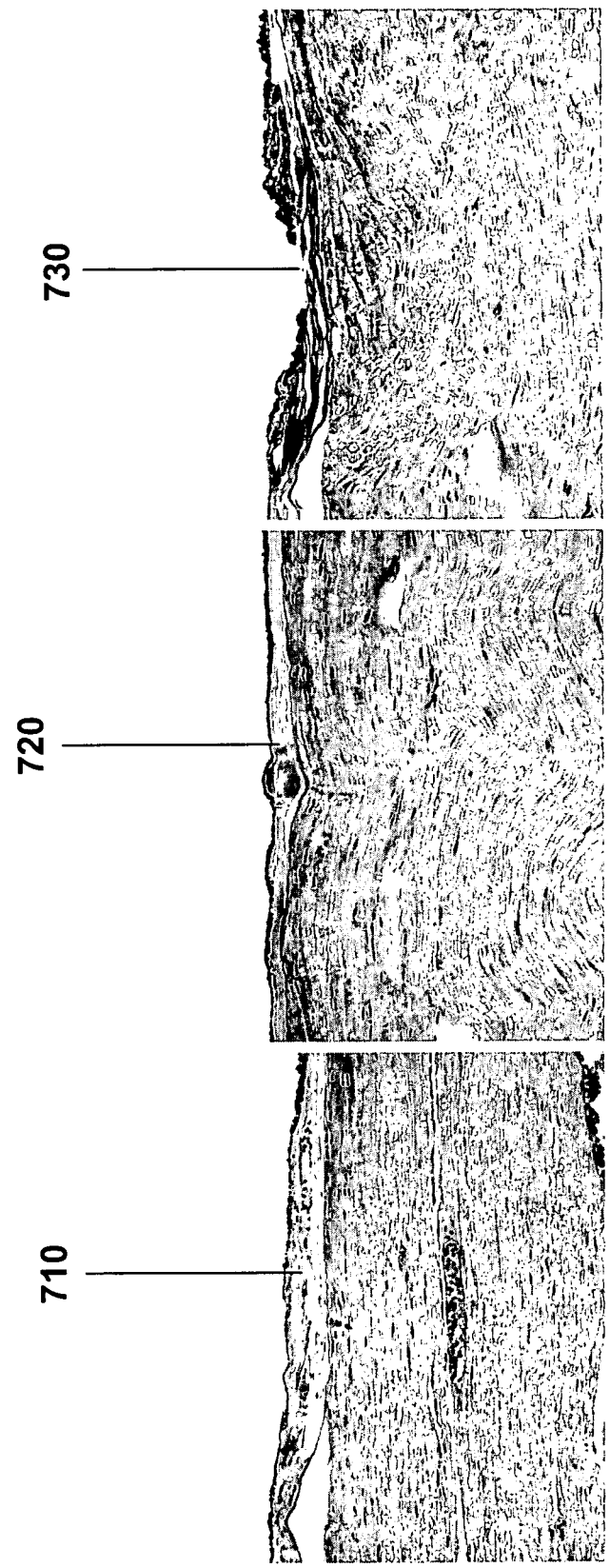
FIG. 7 shows images of the histological samples using H&E stain of rat sciatic nerve tissue (acute): (a) normal tissue (sham) without laser irradiation; (b) experimental stimulation site for 2.1 µm wavelength with 10 pulses above stimulation threshold (0.32 J/cm$^2$) at 0.65 J/cm$^2$; (c) control lesion for 2.12 µm wavelength with 20 pulses at 2.5 J/cm$^2$.

FIG. 7 shows the histological samples using H&E stain of rat sciatic nerve tissue (acute). Normal tissue 710 (sham) without laser irradiation is used as a control. When the tissue is stimulated at the experimental stimulation site for 2.1 μm wavelength with 10 pulses above stimulation threshold (0.32 $J/cm^2$) at 0.65 $J/cm^2$, no obvious damage 720 is observed as compared to a control lesion 730, created by stimulating a normal tissue for 2.12 μm wavelength with 20 pulses at 2.5 $J/cm^2$. The thermal changes sought in the pathological analysis include: collagen hyalinization, collagen swelling, staining changes in coagulated collagen, birefringence image intensity decrease or loss, thermal coagulation of cytoskeleton, disruption and vacuolization of myelin sheaths of nerves, severing of nerves, and thermal coagulation including hyalinization and birefringence changes of collagen in epineurium of nerves [28].

Figure 8:
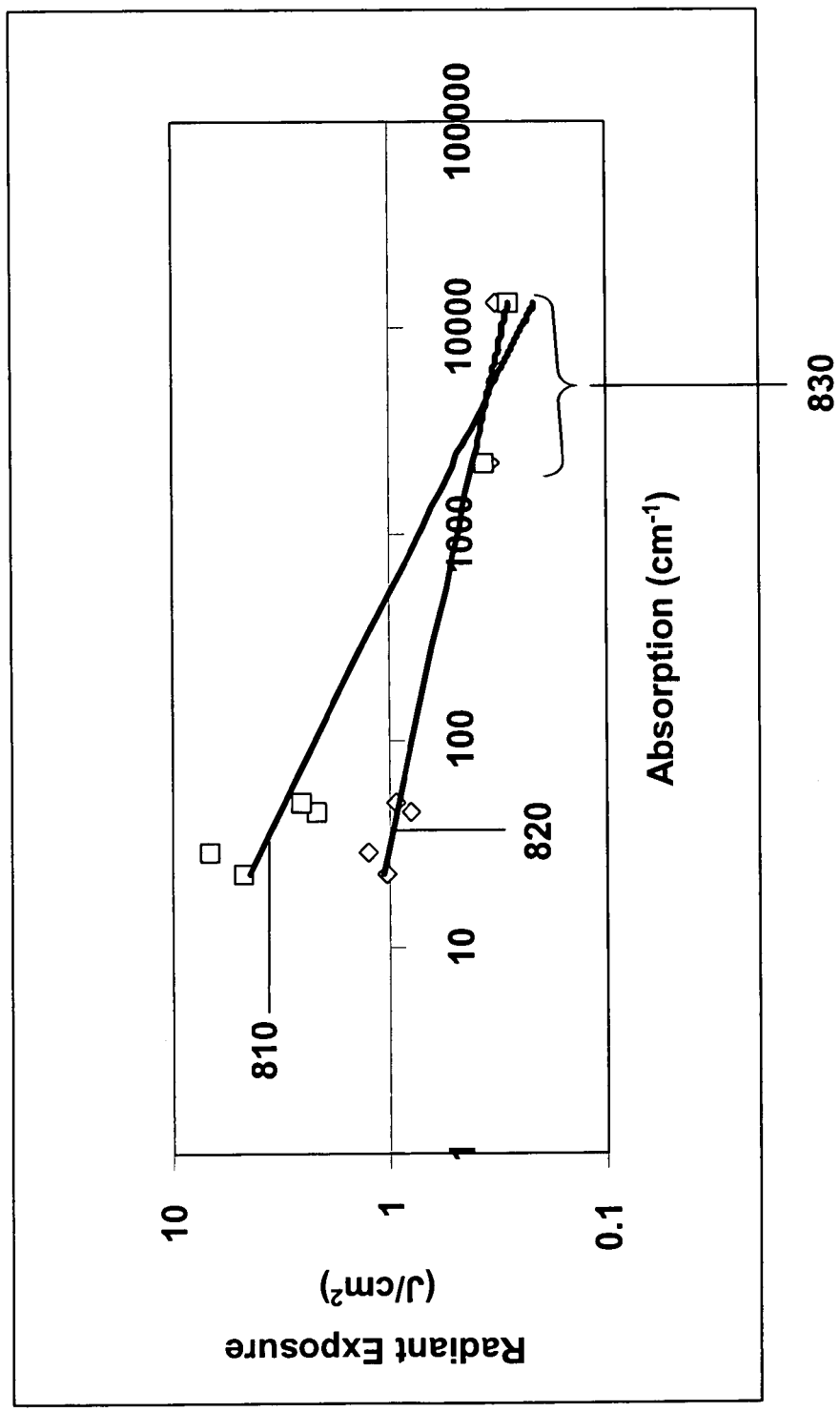
FIG. 8 shows the relationship between stimulation and ablation thresholds and absorption coefficient.

Referring now to FIG. 8, the relationship between the stimulation threshold and absorption coefficient and between the ablation threshold and absorption coefficient are indicated by straight lines 810 and 820, respectively. At high absorption values, the stimulation and ablation thresholds are similar as indicated in the region defined as 830. The stimulation threshold diverges from the ablation threshold as the absorption decreases. Efficiency of stimulation appears as function of penetration depth.

Studies clearly show that optical stimulation is an effective method for stimulation of neural tissue. While the mechanism for this effect is unknown at this time, based on experiments performed thus far, it can be hypothesized that the basis of optical stimulation is a thermo-mechanical effect within the neural tissue. It can be further proposed that the relative contributions of thermal and mechanical mechanisms are dependent on the wavelength used. Studies that elucidate the likely mechanisms of optical stimulation using such methods as patch clamps of specific channels are currently in progress.

Thus, among other things, a novel approach to efficient, artifact-free stimulation of neurons using low-level pulsed infrared laser at radiant exposures well below tissue damage threshold is provided by the present invention. This modality has the potential to change the future of electrophysiology in the laboratory as well as the medical setting. The infinite resolution for spatial selectivity of optical stimulation presents an opportunity for partial nerve resection, currently infeasible with electrical stimulation. The opportunity to map neural function with higher spatial precision than in current practice is presented. Other benefits include contact free stimulation, which reduces the likelihood of physical damage due to the electrodes themselves, as well as infection. At the present time, a commercially manufactured, portable laser operating at an optimal wavelength (Ho:YAG) determined from this study, has been shown to be an effective method for eliciting nerve and muscle potentials. The ability to couple this optimal wavelength through fiber optics helps to significantly reduce the invasiveness for numerous neurosurgical procedures that utilize nerve stimulation. With the immergence of compact and economical solid state lasers, the construction of a self-contained, hand-held device for optical stimulation of nerves during clinical procedures and even an implantable device for future neuroprosthetics may soon become a reality.

While there has been shown several and alternate embodiments of the present invention, it is to be understood that certain changes can be made as would be known to one skilled in the art without departing from the underlying scope of the invention as is discussed and set forth in the specification given above and in the claims given below. Furthermore, the embodiments described above are only intended to illustrate the principles of the present invention and are not intended to limit the scope of the invention to the disclosed elements. Additionally, the references listed herein are incorporated into the application for providing background information only.

LIST OF REFERENCES

[1]. Fritsch, G. and E. Hitzig, Ueber die elektrische Erregbarkeit des Grosshirns. *Archiv Anatomic, Physiologic, and Wissenschaftlische Medicin* 37, 300-32 (1870).

[2]. Geddes, L. A. and Bourland, J. D., Tissue stimulation: theoretical considerations and practical applications. *Med Biol Eng Comput* 23(2), 131-7 (1985).

[3]. Devinsky, O., Electrical and magnetic stimulation of the central nervous system. Historical Overview. *Adv Neurol* 63, 1-16 (1993).

[4]. Pudenz, R. H., Neural stimulation: clinical and laboratory experiences. *Surg Neurol* 39(3), 235-42 (1993).

[5]. Song J. K., Abou-Khalil B., Konrad P. E., Intraventricular monitoring for temporal lobe epilepsy: report on technique and initial results in eight patients. *J Neurol Neurosurg Psychiatry* 74(5), 561-5 (2003).

[6]. Vaquero, J, Manrique, M., Oya, S, & Bravo, G., Tissue damage after chronic cerebellar stimulation. *Acta Neurochirurgica,* 56(3-4), 183-190 (1981).

[7]. Burke, D., et al., Intraoperative monitoring. The International Federation of Clinical Neurophysiology. *Electroencephalogr Clin Neurophysiol Suppl.* 52, 133-48 (1999).

[8]. McGill, K C, Cummins, K L, Dorfman, L J, Berlizot, B B, Leutkemeyer, K, Nishimura, D G, Widrow, B. On the nature and elimination of stimulus artifact in nerve signals evoked and recorded using surface electrodes. *IEEE Trans Biomed Eng.,* 29(2), 129-37 (1982).

[9]. Allegre, G, et al. Cerebral tissue excimer laser photoablation. Preliminary in vivo studies in the rat brain, Proc. SPIE, 1882, 388-392 (1993).

[10]. Cruccu, G and Romaniello, A. Jaw opening reflex after $CO_2$ laser stimulation of the perioral region in man. *Experimental Brain Research,* 118, 564-568 (1998).

[11]. Fork, R. Laser stimulation of nerve cells in aplysia. *Science,* March 5: 907-8 (1971).

[12]. Bragard, D, Chen, A C N, and Plaghki, L. Direct isolation of ultra-late (c-fibre) evoked brain potentials by $CO_2$ laser stimulation of tiny cutaneous surfaces in man. *Neuroscience Letters,* 209, 81-84 (1996).

[13]. Ueno, H, Kaneko, K, Taguchi, T, Fuchigami, Y, Fujimoto, H, Kawai, S. Endoscopic carpal tunnel release and nerve conduction studies. *Int Orthop.* 24(6), 361-3 (2001).

[14]. Roux, F E, Tremoulet, M. Organization of language areas in bilingual patients: a cortical stimulation study. *J Neurosurg.* 97(4), 857-64 (2002).

[15]. Starr, P A. Placement of deep brain stimulators into the subthalamic nucleus or Globus pallidus internus: technical approach. *Stereotact Funct Neurosurg.* 79(3-4), 118-45 (2002).

[16]. Geddes, L. A. and Bourland, J. D. The strength-duration curve. *IEEE Trans Biomed Eng.* 32(6), 458-9 (1985).

[17]. Mountcastle, V, editor. *Medical Physiology,* Vol 1. The C.V. Mosby Company, $13^{th}$ edition (1974).

[18]. Sunderland, S., Anatomical features of nerve trunks in relation to nerve injury and nerve repair. *Clin Neurosurg,* 17, 38-62 (1970).

[19]. Sunderland, S. and Roche, A. F., Axon-myelin relationships in the peripheral nerve fibres. *Acta Anat (Basel),* 33(1-2), 1-37 (1958).

[20]. Kandel, E R, Schwartz, J H, and Jessell, T M, editors. *Principles of Neural Science.* New York: McGraw-Hill, Health Professions Div., $4^{th}$ edition (2000).

[21]. Diott, D & Fayer, M. *J. Opt. Soc. Am. B.* 6(5), 977-994 (1989).

[22]. Edwards, G S, Johnson, B, Kozub, J, Tribble, J & Wagner, K. *Opt, Engng* 32(2), 314-319 (1993).

[23]. Edwards, G S., et al. Tissue ablation by a free-electron laser tuned to the amide II band. *Nature.* 371, 416-419 (1994).

[24]. Izzo A D, Mackanos M A, Beckham J T, Jansen E D. In vivo optical imaging of expression of vascular endothelial growth factor following laser incision in skin. *Lasers Surg Med.* 29(4), 343-50 (2001).

[25]. Cheong W. F., Prahl, S. A, Welch, A. J., A review of the optical properties of biological tissues. IEEE J Quant Electron, 26, 2166-85 (1990).

[26]. Thomsen, S., Identification of lethal injury at the time of photothermal treatment. Laser-Induced Interstital Thremotherapy. Eds. Gerhard Muller and Andre Rogan. SPIE PM 25. Bellingham, Wash. 459-467 (1995).

[27]. Thomsen, S., Pathologic analysis of photothermal and photomechanical effects of laser-tissue interactions. *Photochemistry and Photobiology,* 53(6), 825-835 (1991).

[28]. Thomsen, S., Mapping of thermal injury in biologic tissues using quantitative pathologic techniques. Proc SPIE, 3594, 82-95 (1999).

We claim:

1. A method of optically stimulating tissue of a living subject, comprising the steps of:

delivering, by an optical energy delivery device, optical energy directly to a target tissue at a distance away from the target tissue for a predetermined time period such that the target tissue receives sufficient optical energy to initiate an electrical response within the target tissues, wherein the optical energy is generated in a form of pulses from an energy source and has a wavelength within a range from about 1.2 µm to about 10 µm and a pulse duration within in a range from about 1 µs to about 10 ms;

receiving, at a sensing electrode placed at the target tissue, an electrical signal of the electrical response; and recording and processing, at a computing device, the electrical signal received from the sensing electrode.

2. The method of claim 1, further comprising the step of focusing the optical energy on the target tissue so that the target tissue propagates the electrical response.

3. The method of claim 2, wherein focusing the optical energy occurs in an area with a diameter in a range from 10 µm to 1000 µm.

4. The method of claim 1, wherein the optical energy is delivered in a motion to the target tissue.

5. The method of claim 1, wherein the optical energy is generated by a tunable laser.

6. The method of claim 5, wherein the optical energy is generated by a pulsed infrared laser.

7. The method of claim 6, wherein the optical energy is delivered with a repetition rate no more than 1,000 Hz.

8. The method of claim 6, wherein the optical energy comprises a laser beam with a radiant exposure no more than 5.0 $J/cm^2$.

9. The method of claim 6, wherein the optical energy is generated by an Ho:YAG laser at a wavelength of about 2.12 µm.

10. The method of claim 5, wherein the optical energy has a wavelength of about 4 µm.

11. A method of optically stimulating tissue of a living subject, comprising the steps of:

(a) delivering, by an optical energy delivery device, optical energy directly to a target tissue at a distance away from the target tissue, wherein the optical energy is generated in a form of pulses from an energy source and has a wavelength within a range from about 1.2 µm to about 10 µm and a pulse duration within in a range from about 1 µs to about 10 ms; and (b) focusing the optical energy on the target tissue so that the target tissue propagates an electrical response, wherein in response to a stimulation caused by the optical energy, the target tissue generates an electrical signal without thermal damage in the target tissue, wherein the optical energy has a radiant exposure no more than 10.0 $J/cm^2$, and-wherein the optical energy is focused on an area with a diameter in a range from about 2 µm to about 1000 µm;

(c) receiving, at a sensing electrode placed at the target tissue, the electrical signal; and (d) recording and processing, at a computing device, the electrical signal received from the sensing electrode.

12. The method of claim 11, wherein the optical energy is delivered in a motion to the target tissue.

13. The method of claim 11, wherein the optical energy is delivered to the target tissue for an amount of time sufficient to initiate the electrical response within the target tissue.

14. The method of claim 11, wherein the optical energy is generated by a tunable laser.

15. The method of claim 14, wherein the optical energy is generated by a pulsed infrared laser.

16. The method of claim 14, wherein the optical energy has a wavelength of about 4 µm.

17. The method of claim 15, wherein the optical energy is generated by an Ho:YAG laser at a wavelength of about 2.12 µm.

18. The method of claim 11, wherein the target tissue comprises at least one neural cell in the central nervous system of the living subject.

19. The method of claim 11, wherein the target tissue comprises at least one electrically excitable tissue.

20. The method of claim 11, wherein the optical energy is delivered with a repetition rate no more than 1,000 Hz.

21. The method of claim 11, wherein the optical energy comprises a laser beam with a radiant exposure no more than 5.0 J/cm$^2$.

22. The method of claim 11, wherein the target tissue comprises at least one neural fascicle associated with a peripheral nervous system of the living subject.

23. A method of stimulating tissue of a living subject, comprising the steps of:
delivering, by an optical energy delivery device, at least one beam of radiation directly to a target tissue,
wherein the at least one beam of radiation is generated in a form of pulses from an energy source and has an intensity between a first intensity threshold and a second intensity threshold that is greater than the first intensity threshold;
wherein the at least one beam of radiation comprises optical energy, wherein in response to a stimulation caused by the optical energy, the target tissue generates an electrical signal without thermal damage in the target tissue, wherein the optical energy is focused on an area with a diameter in a range from about 2 μm to about 1000 μm;
wherein the optical energy delivered has a wavelength within a range of between about 1.2 μm to about 10 μm and a pulse duration within in a range from about 1 μs to about 10 ms;
wherein the first intensity threshold is a radiant exposure above which the at least one beam of radiation generates an electrical response in the target tissue; and
wherein the second intensity threshold is a radiant exposure above which the at least one beam of radiation damages the target tissue;
receiving, at a sensing electrode placed at the target tissue, the electrical signal; and
recording and processing, at a computing device, the electrical signal received from the sensing electrode.

24. The method of claim 23, wherein the target tissue comprises at least one neural cell in the central nervous system of the living subject.

25. The method of claim 23, wherein the optical energy is delivered to the target tissue at a distance away from the target tissue.

26. The method of claim 23, wherein the optical energy is delivered to the target tissue for an amount of time sufficient to initiate propagation of the electrical response within the target tissue.

27. The method of claim 23, wherein the target tissue comprises at least one electrically excitable tissue.

28. The method of claim 23, wherein the optical energy is delivered with a repetition rate no more than 1,000 Hz.

29. The method of claim 23, wherein the optical energy comprises a laser beam with a radiant exposure no more than 5.0 J/cm$^2$.

30. The method of claim 23, wherein the optical energy is generated by a tunable laser.

31. The method of claim 30, wherein the optical energy is generated by a pulsed infrared laser.

32. The method of claim 30, wherein the optical energy has a wavelength of about 4 μm.

33. The method of claim 31, wherein the optical energy is generated by an Ho:YAG laser at a wavelength of about 2.12 μm.

34. The method of claim 23, wherein the target tissue comprises at least one neural fascicle associated with a peripheral nervous system of the living subject.

35. The method of claim 23, wherein the at least one beam of radiation is adapted such that the ratio of the damage threshold to the stimulation threshold is in a range from about 1 to about 10.

36. The method of claim 23, wherein the optical energy delivered has a wavelength corresponding to an optical penetration depth in the target tissue.

37. The system of claim 36, wherein the optical penetration depth corresponds to at least one water absorption property associated with the target tissue at the corresponding wavelength.

38. The method of claim 37, wherein the optical penetration depth is about 200 μm.

39. The method of claim 37, wherein the optical energy delivered has a wavelength from about 1.85 μm to 1.88 μm.

* * * * *